United States Patent [19]

Resnick

[11] Patent Number: 4,675,453

[45] Date of Patent: Jun. 23, 1987

[54] PROCESS AND INTERMEDIATES FOR FLUORINATED VINYL ETHER MONOMER

[75] Inventor: Paul R. Resnick, Wilmington, Del.

[73] Assignee: E. I. Du Pont de Nemours and Company, Wilmington, Del.

[21] Appl. No.: 565,777

[22] Filed: Dec. 27, 1983

[51] Int. Cl.$^4$ ............................................. C07C 43/12
[52] U.S. Cl. ................................... 568/615; 568/674; 568/677
[58] Field of Search ................ 560/183, 184; 568/614, 568/615, 674, 677

[56] References Cited

U.S. PATENT DOCUMENTS

| | | | |
|---|---|---|---|
| 4,065,366 | 12/1977 | Oda et al. | 204/98 |
| 4,275,226 | 6/1981 | Yamabe et al. | 560/183 |
| 4,329,434 | 5/1982 | Kimoto et al. | 521/27 |
| 4,348,310 | 9/1982 | Silva et al. | 560/184 |

FOREIGN PATENT DOCUMENTS

| | | | |
|---|---|---|---|
| 41738 | 12/1981 | European Pat. Off. | |
| 0041737 | 12/1981 | European Pat. Off. | 568/615 |

OTHER PUBLICATIONS

Young and Tarrant, "The Preparation of Some Derivatives of Chlorofluoroacetic Acid", *J. Amer. Chem. Soc.*, 71, 2432–2433 (1949).

*Primary Examiner*—James H. Reamer
*Assistant Examiner*—Bruce D. Gray

[57] ABSTRACT

Vinyl ether monomers of the formula

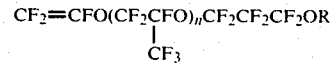

$$CF_2=CFO(CF_2CFO)_nCF_2CF_2CF_2OR$$
$$|$$
$$CF_3$$

wherein n is 0 or 1 and R is $CH_3$ or $C_2H_5$, precursors thereto, and copolymers with, e.g., tetrafluoroethylene, are provided. The copolymers are useful as electrical insulation and as the sheath portion of optical fibers, and can be converted to known ion exchange polymers having carboxylic groups which are useful, e.g., in the form of permionic membrane for separating the compartments of a chloralkali cell. The vinyl ether monomers can also be converted to vinyl ether monomers which contain carboxylate functional groups, which in turn can be copolymerized to useful copolymers.

3 Claims, No Drawings

PROCESS AND INTERMEDIATES FOR FLUORINATED VINYL ETHER MONOMER

BACKGROUND OF THE INVENTION

Fluorinated vinyl monomers have proved to be useful intermediates for making highly fluorinated and perfluorinated polymers and copolymers which are useful, e.g., as electrical insulation, permselective membranes, and the sheath (cladding) layer of optical fibers.

It is an object of this invention to provide novel fluorinated vinyl ether monomers, precursors thereto, and methods for making same.

It is another object of this invention to provide novel highly fluorinated copolymers containing ether linkages.

It is yet another object to provide new and improved methods for making certain known fluorinated vinyl ethers which contain carboxylate functional groups.

It is yet a further object to provide a novel method for making known highly fluorinated and perfluorinated ion exchange polymers which contain carboxylate functional groups.

SUMMARY OF THE INVENTION

According to the present invention, there are provided a chemical compound having the structural formula

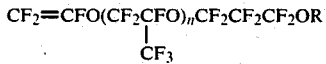

wherein n is 0 or 1 and R is $CH_3$ or $C_2H_5$, copolymers thereof, and precursors thereto.

There are also provided, according to the present invention, improved processes for preparing certain fluorinated vinyl ether monomers which contain carboxylate functional groups.

There is further provided, according to the present invention, a new method for making some fluorinated ion-exchange polymers which contain carboxylate functional groups.

DETAILED DESCRIPTION OF THE INVENTION

The vinyl monomers of the invention can be prepared by a series of steps starting with the known methyl 3-methoxytetrafluoropropionate (see, e.g., U.S. Pat. No. 2,988,537), 3-methoxytetrafluoropropionic acid, or 3-methoxytetrafluoropropionyl fluoride (see, e.g., U.S. Pat. No. 3,113,967). If the free carboxylic acid is used as the starting point, it is first transformed to the acyl fluoride; this can be done, e.g., (1) in two steps by (a) reacting the free acid with any of a variety of reagents such as $PCl_5$, $POCl_3$, $SOCl_2$ or benzoyl chloride at almost any pressure at a temperature of 25° to 250° C. to make 3-methoxytetrafluoropropionyl chloride and (b) reacting the latter with any of a variety of reagents such as alkali metal fluorides or $SbF_3$ with or without a solvent at almost any pressure at a temperature of 50° to 400° C., or (2) in one step by reacting the acid with $SF_4$ at room temperature and autogenous pressure. If the ester is used as the starting point, it is first hydrolyzed to the free carboxylic acid, for example by hydrolysis with acid or base. The acyl fluoride is also directly available by reaction of methyl trifluorovinyl ether and carbonyl fluoride (see J. Amer. Chem. Soc. 84, 4275 (1962)).

The immediate precursors of the vinyl monomers of the invention are prepared by reacting 3-methoxytetrafluoropropionyl fluoride with hexafluoropropylene oxide (HFPO). The reaction is carried out in the presence of fluoride ion catalyst and a reaction medium.

The fluoride ion catalyst is provided by a fluoride compound which dissolves in the reaction medium to the extent of at least 0.001% by weight at 20° C. Suitable fluoride compounds are potassium, rubidium and cesium fluorides. A preferred fluoride compound is potassium fluoride, as its use results in higher yields of the desired product. The fluoride compound can be used in amounts of about 0.01 to 10 equivalents, preferably about 0.05 to 0.5 equivalent, per mole of 3-methoxytetrafluoropropionyl fluoride employed.

The reaction medium can be an aprotic liquid in which the fluoride catalyst is soluble to the extent of at least 0.001% by wt. at 20° C. (component A). Suitable examples include the so-called glymes (mono-, di-, tri- and tetraethyleneglycol dimethyl ether); lactones such as 4-butyrolactone, 5-valerolactone and 6-caprolactone, and mononitriles such as acetonitrile and propionitrile. Triglyme and tetraglyme are preferred because they are more easily separated from the product.

The reaction medium can also be, and preferably is, a mixture of 2 to 50% by volume of component A and 98 to 50% by volume of a second aprotic liquid (component B). Suitable examples of component B include dinitriles such as malono-, succino-, glutaro-, adipo-, methylmalono-, pimelo-, subero-, and phthalo-nitrile; and tetramethylenesulfone. The dinitriles are preferred, and adiponitrile is especially preferred. More preferably, component A constitutes 85 to 98% by volume of the medium, and component B is 15 to 2% by volume. Most preferably, component A constitutes 85 to 95% by volume of the medium, and component B is 5 to 15% by volume.

The reaction of 3-methoxytetrafluoropropionyl fluoride with HFPO is exothermic. Reaction temperatures can range from about 0° to 100° C., with temperatures between 25° and 70° C. being preferred. Pressure is not critical, and subatmospheric and superatmospheric pressures are operable; pressures close to atmospheric are preferred. The pressure in the reaction vessel can be controlled by regulating the rate of supply of gaseous HFPO.

The precursor compounds so made have the structural formula

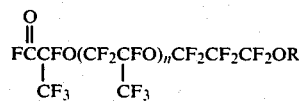

where R is $CH_3$. When 3-methoxytetrafluoropropionyl fluoride reacts with 1 equivalent of HFPO, the precursor compound so made has the indicated structure where n is 0. That precursor compound can in turn react with a second equivalent of HFPO to make the precursor compound where n=1. Small amounts of products wherein more units of HFPO are incorporated are usually also formed. The relative amounts of the precursor compounds where n=0 and n=1 so made can be controlled by controlling the number of equivalents of HFPO used as reactant; relatively lesser amounts of HFPO favor formation of the precursor compound where n=0, and relatively larger amounts of HFPO favor formation of the precursor compound where n=1. If the precursor compounds are made by reacting HFPO with 3-ethoxytetrafluoropropionyl fluoride, the precursor compounds have the indicated structural formula where R is $C_2H_5$.

Such precursor compound is then subjected to a dehalocarbonylation reaction, wherein the elements of $COF_2$ are removed to produce the novel vinyl monomers

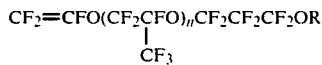

$$CF_2=CFO(CF_2CFO)_nCF_2CF_2CF_2OR$$
$$|$$
$$CF_3$$

where n is 0 or 1 and R is $CH_3$ or $C_2H_5$. This reaction is suitably carried out by contacting the precursor compound with at least one member of the group consisting of $Na_3PO_4$ and $Na_2CO_3$ at a temperature of at least 170° C., preferably 190° to 260° C.

These vinyl ether monomers can be copolymerized with other fluorinated monomers to make novel copolymers. Suitable comonomers include $CX_2=CX_2$ where the four X's are four fluorines or three fluorines and one chlorine. Such copolymers comprise about 70 to 95 mol % $-CX_2-CX_2-$ units where the four X's are as defined above, and about 5 to 30 mol % of substituted ethylene units of the formula

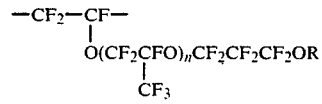

$$-CF_2-CF-$$
$$|$$
$$O(CF_2CFO)_nCF_2CF_2CF_2OR$$
$$|$$
$$CF_3$$

wherein n is 0 or 1 and R is $CH_3$ or $C_2H_5$, the substituted ethylene units being randomly positioned throughout the copolymer chain. The copolymers wherein the four X's are four fluorines are preferred. These copolymers are useful, e.g., as insulation on electrical conductors, base for printed circuits, and as the sheath (cladding) portion of optical fibers.

The copolymers can be prepared by general polymerization techniques developed for homo- and copolymerizations of fluorinated ethylenes, particularly those employed for tetrafluoroethylene which are described in the literature. Nonaqueous techniques for preparing the copolymers include that of U.S. Pat. No. 3,041,317, that is, by the polymerization of a mixture of the major monomer therein, such as tetrafluoroethylene, and the fluorinated vinyl ether monomer in the presence of a free radical initiator, preferably a peroxydicarbonate, a perfluorocarbon peroxide or azo compound, at a temperature in the range 0°-200° C. and at pressures in the range of $10^5$ to $2 \times 10^7$ pascals (1-200 Atm.) or higher. The nonaqueous polymerization may, if desired, be carried out in the presence of a fluorinated solvent. Suitable fluorinated solvents are inert, liquid, perfluorinated hydrocarbons, such as perfluoromethylcyclohexane, perfluorodimethylcyclobutane, perfluorooctane, perfluorobenzene and the like, and inert, liquid chlorofluorocarbons such as 1,1,2-trichloro-1,2-2-trifluoroethane, and the like.

Aqueous techniques can also be used for preparing the copolymer, and include contacting the monomers with an aqueous medium containing a free-radical initiator to obtain a slurry of polymer particles in non-water-wet or granular form, as disclosed in U.S. Pat. No. 2,393,967, or contacting the monomers with an aqueous medium containing both a free-radical initiator and a telogenically inactive dispersing agent, to obtain an aqueous colloidal dispersion of polymer particles, and coagulating the dispersion, as disclosed, for example, in U.S. Pat. No. 2,559,752 and U.S. Pat. No. 2,593,583.

The above copolymers can, if desired, be converted to esters of known fluorinated ion-exchange polymers by treatment with a strong acid at a temperature of at least 50° C. but below the decomposition temperature of the above-described copolymers, the product ion-exchange polymers, and the strong acid. The strong acids which are suitable for treatment of the above copolymers to make fluorinated ion-exchange copolymers or precursors thereto are suitably, e.g., $H_2SO_4$, $ClSO_3H$, $FSO_3H$ or $R_fSO_3H$ where $R_f$ is a perfluorinated $C_1$ to $C_8$ group, or Lewis acids in which the halide is fluoride such as $SbF_5$. Temperatures of 80° to 150° C. are preferred. Such treatment of the above copolymers gives copolymers comprising about 70 to 95 mol % $-CX_2-CX_2-$ units wherein the four X's are four fluorines or three fluorines and one chlorine, and about 5 to 30 mol % of substituted ethylene units of the formula

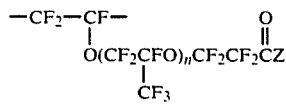

$$-CF_2-CF- \quad O$$
$$| \quad ||$$
$$O(CF_2CFO)_nCF_2CF_2CZ$$
$$|$$
$$CF_3$$

where n is 0 or 1, Z is F or OR', and R' is at least one member of the group consisting of R and H, the substituted ethylene units being randomly positioned throughout the copolymer chain. The carboxylic ester polymers can be hydrolyzed to known carboxylic acid polymers which are useful for ion-exchange purposes. Some hydrolysis of the ester polymers may occur to varying degree during the treatment of the ether-containing polymers with strong acid, the amount of hydrolysis varying with the acid and conditions used.

Such fluorinated polymers which contain carboxylic acid functional groups can be employed in various known ion-exchange uses. One such use is in the form of a permselective membrane for separating the anode and cathode compartments of a chloralkali electrolysis cell; the ion-exchange capacity of the polymer for such use should be in the range of 0.7 to 1.5 meq/g (milliequivalents/gram), preferably 0.8 to 1.3 meq/g.

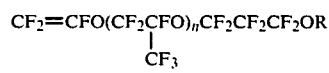

$$CF_2=CFO(CF_2CFO)_nCF_2CF_2CF_2OR$$
$$|$$
$$CF_3$$

or their bromine adducts

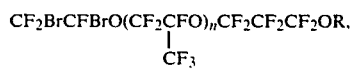

$$CF_2BrCFBrO(CF_2CFO)_nCF_2CF_2CF_2OR,$$
$$|$$
$$CF_3$$

i.e., compounds of the formula

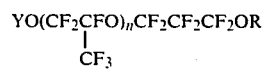

$$YO(CF_2CFO)_nCF_2CF_2CF_2OR$$
$$|$$
$$CF_3$$

wherein Y is $CF_2=CF-$ or $CF_2BrCFBr-$, can also be converted respectively to vinyl ether monomers which contain carboxylic ester functional groups, having the structural formula

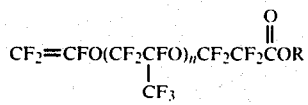

or their bromine adducts

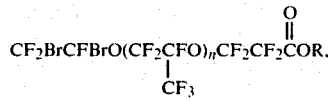

i.e., compounds of the formula

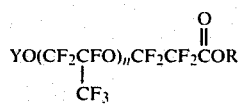

wherein Y is $CF_2=CF-$ or $CF_2BrCFBr-$, n is 0 or 1, and R is $CH_3$ or $C_2H_5$. When Y is $CF_2=CF-$, this conversion is suitably carried out by treatment with a strong acid at a temperature of at least 25° C., but below the decomposition temperatures of both the starting vinyl ether monomer and the product vinyl carboxylic ester monomer and the strong acid, preferably at 70° to 100° C.; above about 100° C., some decomposition of the vinyl ether compound may occur. When Y is $CF_2BrCFBr-$, the conversion is suitably carried out by treatment with a strong acid at a temperature of at least 25° C., but below the decomposition temperatures of both the starting brominated ether compound and the product brominated carboxylic ester compound and the strong acid, preferably at 100° to 150° C. The strong acids which are suitable for treatment of the vinyl ether monomers or their bromine adducts to make compounds containing carboxylic ester functional groups are suitably, e.g., $H_2SO_4$, $ClSO_3H$, $FSO_3H$ or $R_fSO_3H$ where $R_f$ is a perfluorinated $C_1$ to $C_8$ group. The resulting vinyl monomers containing carboxylic ester groups can be copolymerized with other fluorinated ethylenically unsaturated monomers, such as $CX_2=CX_2$ where X is as defined hereinabove, to provide copolymers which can be hydrolyzed to the known fluorinated carboxylic acid ion exchange polymers referred to above.

The bromine adducts are suitably made by reaction of bromine with the vinyl ether monomers. Addition of bromine to the olefinic bond is facilitated by irradiation with ultraviolet and/or visible light, as from a commercially available sun lamp. An inert solvent can be used but is not necessary.

The bromine adduct of the vinyl ether monomer which contains a carboxylic ester functional group can suitably be debrominated to the vinyl ether monomer which contains a carboxylic ester functional group by, e.g., treatment with zinc.

Preparation of the vinyl ether monomer which contains a carboxylic ester functional group via the three step route of brominating the vinyl ether monomer, acid treatment to convert the $-CF_2OR$ moiety to the $-COOR$ group, and debromination, is particularly advantageous because the brominated compound is more thermally stable than the vinyl ether compound.

Although that vinyl monomer with carboxylic ester group, referred to in the previous paragraph, where n is 0 and R is $CH_3$, i.e.,

is a known compound, the method disclosed herein for making it according to the present invention is superior to a known method, the dehalocarbonylation of

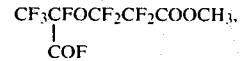

due to a sequence of reactions in the known method starting with cyclization to form

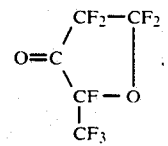

which known method yields but little of the desired vinyl carboxylic ester monomer. It is also superior to another known method which starts with epoxidation of 1,1,2,3,3-pentafluoro-3-chloropropene-1. The method disclosed herein, ending with treatment of the vinyl ether monomer with strong acid, provides an overall yield of about 50% for the four steps starting from

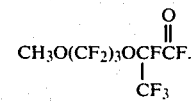

To further illustrate the innovative aspects of the present invention, the following examples are provided.

EXAMPLES

All temperatures specified herein are in °C.

EXAMPLE 1

A. Preparation of $CH_3OCF_2CF_2COOH$ (3-Methoxytetrafluoropropionic Acid)

A mixture of 32 g sodium hydroxide, 400 g water and 152 g methyl 3-methoxytetrafluoropropionate was stirred at room temperature until a single liquid layer was obtained. The product was acidified with 37% aqueous HCl and the lower layer separated. The aqueous layer was extracted four times with 50 ml ethyl ether and the combined ether extracts and lower layer distilled to give 103.3 g (73.4%) 3-methoxytetrafluoropropionic acid, b.p. 85°–86° at 20 mm.

B. Preparation of $CH_3OCF_2CF_2COCl$ (3-Methoxytetrafluoropropionyl Chloride)

A mixture of 47.4 g 3-methoxytetrafluoropropionic acid and 67.3 g phosphorous pentachloride was heated and the contents distilled to obtain a pale yellow liquid boiling to 102°. Redistillation of this liquid yielded 49.8 g (95.2%) 3-methoxytetrafluoropropionyl chloride, b.p. 84°–86°.

C. Preparation of CH₃OCF₂CH₂COF (3-Methoxytetrafluoropropionyl Fluoride)

A mixture of 34.8 g potassium fluoride, 100 ml tetramethylene sulfone and 49.8 g 3-methoxytetrafluoropropionyl chloride was slowly heated to give 35.4 g of colorless liquid (77.8%) whose infrared spectrum was identical to 3-methoxytetrafluoropropionyl fluoride.

D. Preparation of

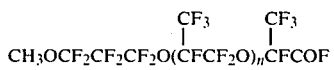
CH₃OCF₂CF₂CF₂O(CFCF₂O)ₙCFCOF where n=0 and 1.
(2-(3-Methoxyhexafluoropropoxy)tetrafluoropropionyl fluoride and
2-[2-(3-Methoxyhexafluoropropoxy)hexafluoropropoxy]tetrafluoropropionyl fluoride)

A mixture of 1.5 g potassium fluoride, 56 g of a 9/1 volume/volume mixture of adiponitrile and tetraglyme and 44.3 g of 3-methoxytetrafluoropropionyl fluoride were reacted at 30° with 44 g of hexafluoropropylene oxide. The lower layer of the reaction mixture was separated and distilled to give 28.6 g (49%) of the product where n=0, b.p. 50° at 100 mm, and 23.0 g (26%) of the product where n=1, b.p. 90° at 100 mm.

EXAMPLE 2

Preparation of CH₃OCF₂CF₂CF₂OCF=CF₂(3-Methoxyhexafluoropropyltrifluoroethenyl ether)

A glass tube (2.5 cm diameter) packed with 125 g of dry trisodium phosphate was heated to 225° and 30.4 g 2-(3-methoxyhexafluoropropoxy)tetrafluoropropionyl fluoride was passed through it at a rate of 0.48 ml per minute. The crude product was distilled to give 17.0 g 3-methoxyhexafluoropropyltrifluoroethenyl ether, b.p. 54° at 200 mm, whose structure was consistent with its infrared spectrum and ¹H and ¹⁹F NMR spectra.

EXAMPLE 3

Preparation of

CH₃OCF₂CF₂CF₂OCFCF₂OCF=CF₂

A tube containing 125 g of dry trisodium phosphate was heated to 225° and 19.8 g

CH₃OCF₂CF₂CF₂OCFCF₂OCFCOF added at a rate of 0.48 ml per minute. The crude product was distilled to give 10.8 g

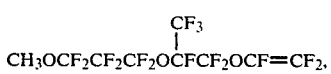
CH₃OCF₂CF₂CF₂OCFCF₂OCF=CF₂, b.p. 80°–82° at 100 mm, whose structure was consistent with its infrared and ¹⁹F NMR spectra.

For purposes of further confirming the structure of the product, a small portion of the above vinyl ether was reacted with excess bromine under irradiation of a "GE Sun Lamp." The crude product was washed with aqueous sodium bisulfite and distilled to give

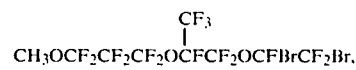
CH₃OCF₂CF₂CF₂OCFCF₂OCFBrCF₂Br, b.p. 196°, whose structure was consistent with its infrared and ¹⁹F NMR spectra.

EXAMPLE 4

Preparation of

CF₂=CFOCF₂CFOCF₂CF₂COOCH₃

A mixture of 10.0 g

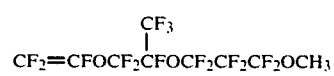
CF₂=CFOCF₂CFOCF₂CF₂CF₂OCH₃ and 10.8 g 96% sulfuric acid was stirred at room temperature for 16 hours. The mixture was added to 100 ml water, and 9.3 g of a lower layer, almost all starting material, was recovered. The 9.3 g recovered material was heated at 80° for 16 hours with 15 ml 96% sulfuric acid and the mixture added to 50 ml water to give 7.8 g product. Gas chromatographic analysis showed the product to contain 74% starting material and 21%

CF₂=CFOCF₂CFOCF₂CF₂COOCH₃.

For purposes of confirming the structure of the product, a portion of the product was brominated to give material containing

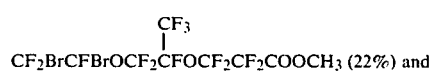
CF₂BrCFBrOCF₂CFOCF₂CF₂COOCH₃ (22%) and

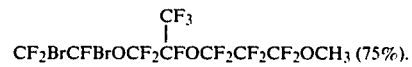
CF₂BrCFBrOCF₂CFOCF₂CF₂CF₂OCH₃ (75%).

The gas chromatographic retention times of these products were identical to those of authentic samples. The IR spectrum of the mixture showed an absorption at 5.6 microns (COOCH₃). The ¹H NMR showed two signlets at 3.52 ppm (CH₃OCF₂CF₂CF₂—) and 3.74 ppm

(CH₃OCCF₂CF₂—), in the ratio of 1/3.36 while the ¹⁹F NMR was consistent with a mixture of

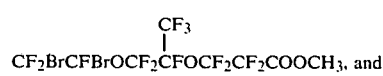
CF₂BrCFBrOCF₂CFOCF₂CF₂COOCH₃, and

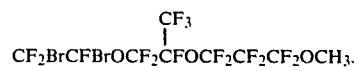
CF₂BrCFBrOCF₂CFOCF₂CF₂CF₂OCH₃.

The remainder of the reaction product was heated at 100° for 4 hours and then added to 50 ml water to give 4.5 g of product which contained 51% starting material and 38% product. An infrared spectrum of the material corresponding to the 38% product peak was identical to that of an authentic sample of $$CF_2=CFOCF_2\underset{\underset{CF_3}{|}}{C}FOCF_2CF_2COOCH_3.$$

EXAMPLE 5

A. Preparation of $CF_2BrCFBrOCF_2CF_2CF_2OCH_3$.

A 4.7 g mixture of $CF_2=CFO(CF_2)_3OCH_3$ (ca. 70 mol %) and $CClF_2CCl_2F$ (ca. 30 mol %) was reacted with excess bromine under irradiation of a GE Sun Lamp. The excess bromine was destroyed with aqueous sodium bisulfite, and the product (lower layer, 4.2 g) was identified by gas chromatographic and NMR analyses to be $CF_2BrCFBrOCF_2CF_2CF_2OCH_3$ containing a trace of $CClF_2CCl_2F$.

B. Preparation of $CF_2BrCFBrOCF_2CF_2COOCH_3$.

A mixture of 4.2 g $CF_2BrCFBrOCF_2CF_2CF_2OCH_3$ and 25 ml 96% sulfuric acid was heated at 120° for 4 hours and stirred at room temperature for 16 hours. The reaction mixture was added to 200 ml cold water and the lower layer separated. The aqueous layer was extracted with $CClF_2CCl_2F$, and gas chromatographic and NMR analysis showed the presence of $CF_2BrCFBrOCF_2CF_2COOCH_3$ and $CClF_2CCl_2F$ as the only halogenated compounds.

C. Preparation of $CF_2=CFOCF_2CF_2COOCH_3$.

When 29.2 g $CF_2BrCFBrOCF_2CF_2COOCH_3$ in 5 ml tetraglyme was added to 6.5 g zinc dust, 0.1 g iodine and 40 ml tetraglyme, an exothermic reaction was observed. The reaction mixture was distilled at 100 mm Hg pressure to give 15.1g (84% yield) $CF_2=CFOCF_2CF_2COOCH_3$ whose structure was confirmed by comparison of its infrared spectrum and gas chromatographic retention time with those of an authentic sample.

EXAMPLE 6

Copolymerization of $CH_3OCF_2CF_2CF_2OCF=CF_2$ and Tetrafluoroethylene.

A mixture of 17.0 g $CH_3OCF_2CF_2CF_2OCF=CF_2$, 35.0 g 1,1,2-trifluoro-1,2,2-trichloroethane (F113), 0.02 g bis (4-t-butylcyclohexyl)peroxydicarbonate and 0 g tetrafluoroethylene was heated at 45° for one hour and 50° for three hours to give a polymeric gel. The polymer, 6.5 g, was isolated by washing three times with methanol and drying. The infrared spectrum of a thin film pressed at 300° was consistent with a copolymer of tetrafluoroethylene and $CH_3OCF_2CF_2CF_2OCF=CF_2$. The $^{19}F$ NMR spectrum of the copolymer was also consistent with this structure and showed that the molar ratio of $CF_2=CF_2$ to $CH_3OCF_2CF_2CF_2OCF=CF_2$ was 5.06 to 1.00.

EXAMPLE 7

Copolymerization of $$CH_3OCF_2CF_2CF_2O\underset{\underset{CF_3}{|}}{C}FCF_2OCF=CF_2$$

and Tetrafluoroethylene.
A mixture of 10.7 g $$CH_3OCF_2CF_2CF_2O\underset{\underset{CF_3}{|}}{C}FCF_2OCF=CF_2,$$

20 g 1,1,2-trifluoro-1,2,2-trichloroethane (F113), 0.02 g bis (4-t-butylcyclohexyl)peroxydicarbonate and 15 g tetrafluoroethylene was heated at 45° for one hour and 50° for three hours to give a colorless gel. A white polymer, 1.8 g, was isolated by washing three times with methanol and drying. The infrared spectrum of a thin film pressed at 275° was consistent with a copolymer of tetrafluoroethylene and $$CH_3OCF_2CF_2CF_2O\underset{\underset{CF_3}{|}}{C}FCF_2OCF=CF_2.$$

The $^{19}F$ NMR spectrum was also consistent with this structure and showed the molar ratio of tetrafluoroethylene to $$CH_3OCF_2CF_2CF_2O\underset{\underset{CF_3}{|}}{C}FCF_2OCF=CF_2$$

to be 6.50 to 1.00.

EXAMPLE 8

Hydrolysis of $CF_2=CF_2/CF_2=CFOCF_2CF_2CF_2OCH_3$ Copolymer and Use of Hydrolyzed Copolymer in a Chloralkali Cell.

A mixture of 25 ml chlorosulfonic acid and 2.3 g of a copolymer of $CF_2=CF_2$ and $CF_2=CFOCF_2CF_2CF_2OCH_3$ was stirred and heated for 5 hours at 100°. The reaction mixture was carefully added to 500 ml ice and ice water and the polymer recovered by filtration. The polymer was heated in 30 ml refluxing anhydrous methanol for 16 hours, filtered and dried. A thin film of the product could be pressed at 300° whose infrared spectrum was identical to that of a film of copolymer prepared by the copolymerization of $CF_2=CF_2$ and $CF_2=CFOCF_2CF_2COOCH_3$.

A larger film of the material was pressed at 310°. It was hydrolyzed in a mixture of 300 ml water, 375 g methanol and 75 ml 10N sodium hydroxide at 60° for 66 hrs to give a film of the corresponding sodium salt 7.6 mils in thickness. The film was mounted in a chloralkali cell and produced 31.3% NaOH with a current efficiency of 94.2% at 4.34 volts.

I claim:
1. A chemical compound having the structural formula

$$CF_2BrCFBrO(CF_2\underset{\underset{CF_3}{|}}{C}FO)_nCF_2CF_2CF_2OR$$

wherein n is 0 or 1 and R is $CH_3$ or $C_2H_5$.

2. The compound of claim 1 wherein n is 0 and R is $CH_3$.

3. The compound of claim 1 wherein n is 1 and R is $CH_3$.

* * * * *